United States Patent [19]

Sohn et al.

[11] Patent Number: 4,855,088
[45] Date of Patent: Aug. 8, 1989

[54] BUBBLE GENERATOR AND METHOD

[75] Inventors: Chul H. Sohn, Irvine; David L. Goodale, Anaheim, both of Calif.

[73] Assignee: Beckman Instruments, Inc., Fullerton, Calif.

[21] Appl. No.: 262,248

[22] Filed: Oct. 20, 1988

Related U.S. Application Data

[63] Continuation of Ser. No. 67,034, Jun. 26, 1987, abandoned.

[51] Int. Cl.⁴ .............................. B01F 3/04
[52] U.S. Cl. .................... 261/53; 261/64.3; 261/DIG. 74; 137/495; 137/605
[58] Field of Search ............. 261/64.3, 53, DIG. 74; 137/605, 495

[56] References Cited

U.S. PATENT DOCUMENTS

| 474,414 | 5/1892 | Schneible | 261/64.3 |
|---|---|---|---|
| 1,338,592 | 4/1920 | Sanford | 261/64.3 |
| 2,894,712 | 7/1959 | Booth et al. | 251/16 |
| 3,077,341 | 2/1963 | Schlichting | 261/DIG. 38 |
| 3,361,161 | 1/1968 | Schwartz | 261/53 |
| 3,391,909 | 7/1968 | Sarto | 261/DIG. 38 |
| 3,478,776 | 11/1969 | Royer | 137/495 |
| 3,923,079 | 12/1975 | Hughes et al. | 137/495 |
| 4,064,891 | 12/1977 | Eberhardt | 137/605 |
| 4,376,739 | 3/1983 | Passey, Jr. | 261/DIG. 38 |
| 4,534,914 | 8/1985 | Takahashi et al. | 261/64.3 |

FOREIGN PATENT DOCUMENTS

| 465762 | 9/1928 | Fed. Rep. of Germany | 261/64.3 |
|---|---|---|---|
| 398491 | 9/1933 | United Kingdom | 261/64.3 |

*Primary Examiner*—Tim Miles
*Attorney, Agent, or Firm*—William H. May; Arnold Grant; Gary T. Hampson

[57] ABSTRACT

A device for generating a plurality of gas bubbles in a liquid. The device includes a conduit adapted to carry the liquid. A first gas chamber is formed near the conduit and an orifice proximate a side wall of the conduit defines a passageway between the first gas chamber and the conduit. A valve member is adapted to seat against and close the orifice. The device may include a second gas chamber and a diaphragm responsive to gas pressure in the second gas chamber. A conduit connecting the first and second chambers may include a variable vent for controlling the size and number of gas bubbles injected into the liquid flowing in the conduit.

31 Claims, 1 Drawing Sheet

BUBBLE GENERATOR AND METHOD

This application is a continuation, of application Ser. No. 067,034, filed June 26, 1987, now abandoned.

FIELD OF THE INVENTION

The present invention relates to the field of fluid control and more particularly to the generation of gas bubbles in a liquid stream.

BACKGROUND OF THE INVENTION

It is known, for example, in the automated clinical chemistry analyzer art, to utilize liquid handling probes for moving liquid samples and/or reagents among various containers. Typically, liquid handling probes include an open-ended pipetting probe coupled to an automatically-controlled motor-driven syringe-type pump. The probe is lowered into liquid held in a container and a volume of liquid is drawn into the probe by operating the syringe-type pump. The probe is withdrawn from the container and is moved to a position above or within a second container such as a reaction cuvette or cell. Once so positioned, the syringe-type pump is operated again to dispense liquid from the probe into the reaction cell.

A common problem associated with liquid handling probes is carryover. Carryover occurs when, for example, a first reagent is transferred by a probe from a reagent storage container to a reaction cell and, during the next liquid transfer operation, a second different reagent is transferred by the same probe from a second reagent container to the reaction cell. Traces of the first reagent may remain in or on the probe and be carried over to and contaminate the second reagent as it is drawn into and expelled from the probe during the second transfer operation. Such carryover can result in errors in the analysis of samples, a particularly troubling result where the samples are human body fluid samples used in the evaluation and/or treatment of various diseases or disorders.

In order to reduce carryover, it is known to wash the exterior of a probe by dipping the contaminated end portion of the probe into a wash cell filled with a suitable wash liquid, such as deionized water. The wash liquid may be circulated through the wash cell and thus around the exterior of the probe to more thoroughly cleanse the probe exterior. Similarly, it is known to flow wash liquid through the probe. Preferably, the wash liquid is segmented by entrained gas bubbles that tend to scrub the probe interior surface as the bubbles pass, further enhancing the removal of carryover substances.

Several approaches have been utilized for entraining scrubbing gas bubbles in the wash liquid that flows through the probe. One approach has been to repeatedly insert and remove the open end of the probe into wash liquid as the wash liquid is being aspirated by the probe. This produces a number of gas bubbles that are drawn into the probe which are then expelled from the probe into a suitable wash cell or receptacle.

Another known approach is to inject gas bubbles into the wash liquid as it flows through a conduit leading to the probe. Pressurized gas is supplied to a solenoid operated valve which is in turn connected to the conduit carrying the wash liquid. While the wash liquid flows through the conduit, a signal is applied to the valve to rapidly cycle the valve on and off. Each on-off cycle introduces a gas bubble into the wash liquid flow. The gas bubbles are carried by the wash liquid flow to and through the probe, producing the desired scrubbing action.

However, both of these bubble generating techniques approaches have drawbacks. Mechanically cycling the end of a probe into and out of a wash liquid to thereby aspirate gas bubbles is time consuming and limits the size and number of bubbles that may be introduced into the probe. Consequently, probe washing may be compromised, resulting in increased carryover from one transfer operation to the next.

The bubble injection approach, on the other hand, requires an electronic drive circuit that controls the valve. Any changes in gas bubble size or number must be controlled by varying the frequency and duty cycle of the pulsed signal applied to the valve, thereby increasing the complexity of the electronic control circuitry. In any event, most such valves can operate at no more than 100 cycles per second, thus limiting the number of bubbles injected into the liquid flow to 100 bubbles/second.

The bubble injection approach also requires frequent replacement of the solenoid valve. Such a valve may be required to cycle almost 200,000 times during a typical operating day of an automated analyzer. Solenoid valves of the type used in these bubble injection applications have at most a ten million cycle life. Thus, the valves must be replaced at least every two months. Each replacement is expensive and requires that the analyzer be shut down, a problem where the analyzer is one of the primary analytical tools in a hospital clinical chemistry laboratory.

Furthermore, the solenoid valve or the conduit connecting the valve to the wash liquid conduit holds a volume of liquid that is not directly in the wash liquid flow path. This liquid volume represents a dead volume in which reagents or samples drawn into the probe may become trapped, substantially reducing the effectiveness of the wash liquid and gas bubbles. Gas bubbles can also become trapped in the dead volume. Because the gas bubbles are compressible as compared to liquid, the metering accuracy of the liquid delivered by the syringe-type pump can be adversely influenced.

Thus, there is a need for a simple bubble generator which can rapidly inject bubbles into a wash liquid flow. The bubble generator should be reliable and easily adjustable to vary bubble size and spacing while eliminating the electronic circuitry required to operate the rapid cycling valve described above. Furthermore, it is desirable to eliminate or substantially reduce dead volume present in prior art systems.

SUMMARY OF THE INVENTION

The present invention overcomes the limitations and drawbacks characteristic of the prior art devices. A bubble generating device in accordance with the present invention includes a conduit adapted to carry a liquid. The device includes a gas chamber near the conduit and an orifice formed proximate a wall of the liquid conduit. The orifice defines a passageway between the gas chamber and the conduit. A valve member is adapted to seat against and close the orifice. A gas inlet is formed in the device to connect the gas chamber to a supply of pressurized gas.

The device may further include an actuating mechanism for moving the valve member between a closed position wherein the valve member seats against and closes the orifice and an open position wherein the valve member opens the passageway between the first gas chamber and the conduit. The actuating mechanism may include a second upper gas chamber and a diaphram responsive to gas pressure in the second chamber. The diaphram is coupled to the valve member, moving the valve member between the closed and opened positions in response to pressurized gas introduced into the second chamber. A suitable means such as a spring biases the valve member towards the closed position.

A conduit may be formed between the gas inlet of the first chamber and the second chamber. A flow restrictor and variable vent connected to the conduit allow gas flowing in the conduit to be bled away thereby controlling gas pressure present within the first chamber. A simple solenoid operated air valve may be used to supply pressurized gas to the second chamber, thereby simultaneously actuating the diaphragm, opening the orifice and providing a controlled gas flow to the first chamber. With the orifice open, the pressurized gas in the first chamber may be introduced through the orifice into liquid flowing through the liquid-carrying conduit.

Because the orifice is formed at or very near the side wall of the liquid conduit, the device of the present invention minimizes dead volume as compared to prior art devices. Furthermore, the bubble generating device of the present invention eliminates the need for complex electronic circuitry associated with the prior art air valve device. The simple, inexpensive and easily utilized solenoid valve supplying pressurized gas to the second chamber is not subject to the rapid wear experienced with the prior air valve device. Furthermore, by adjusting the flow of gas through the variable vent, the dynamics of the gas flow through the orifice into the liquid flowing within the liquid conduit may be easily and rapidly varied. Thus, a wide range of bubble size and population can be produced within a given segment of liquid as it flows through the liquid conduit.

Accordingly, the bubble generating device of the present invention is simple and reliable and is easily controlled by a simple on-off electric signal applied to a correspondingly simple gas control solenoid.

DETAILED DESCRIPTION OF THE INVENTION

Figure 1:
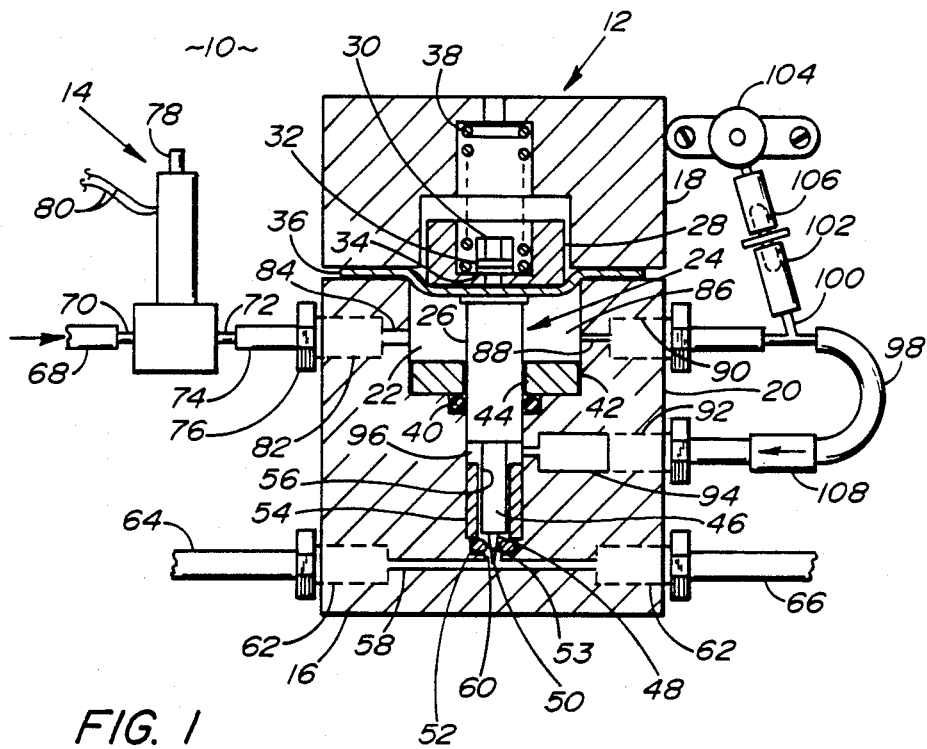
FIG. 1 illustrates a device of the present invention shown in partial cross section.

With reference to FIG. 1, a bubble generating device 10 in accordance with the present invention includes a bubbler or bubble injector 12 and a solenoid operated three-way gas valve 14. The bubble injector 12 includes a body 16 comprising an upper portion 18 and a lower portion 20 fixed together by suitable fasteners such as screws (not shown). The body 16 may be formed from a clear plastic material such as acrylic so as to provide ready visual inspection of the operation of the device 10.

With the upper and lower portions 18 and 20 assembled as illustrated in FIG. 1, the body 16 defines an internal cavity 22. The cavity 22 comprises a plurality of cylindrical portions of different diameters. Disposed within the cavity 22 is a piston 24 including a shaft 26. A cup-shaped piston head 28 is fixed to the upper end of the shaft 26 by means of a cap screw 30. The cap screw 30 passes through a washer 32, a split washer 34, and the piston head 28 and is threaded into the top of the shaft 26. A flexible diaphragm 36 is secured between the piston head 28 and shaft 26. The periphery of the diaphragm 36 is held securely between the upper and lower portions 18 and 20. A spring 38 is disposed between an upper surface of the cavity 22 and the washer 32 within the piston head 28.

An O-ring 40 provides a seal between the shaft 26 and the cavity 22. The O-ring 40 is held in place by an annular retainer 42 which may be pressed or cemented into place. The retainer 42 includes a central opening 44 therein through which the shaft 26 passes and which acts as a guide for the shaft 26.

The shaft 26 includes a reduced lower portion 46 and, at the lower end thereof as viewed in FIG. 1, a conical tip 48 tapering to a point 50. A ring-shaped seal 52 defining an orifice 53 and having a four lobe design such as a Quad-X seal available from Minnesota Rubber Company (hereinafter referred to as a Q-ring) is retained at the lower end of the cavity 22 by means of a cylindrical retainer 54 which may be pressed or cemented into place. As with the retainer 42, the retainer 54 includes a central opening 56 formed therethrough which allows free passage of the reduced lower portion 46. The clearance between the central opening 56 and the reduced lower portion 46 is sufficient to allow gas to flow therebetween.

Figure 2:
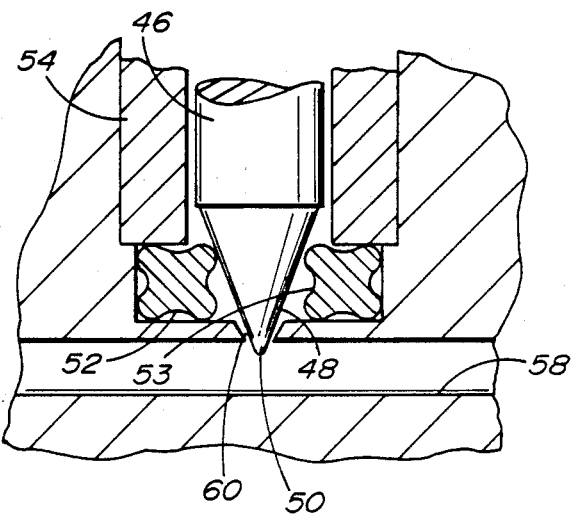
FIG. 2 is an enlarged view of the bubble forming orifice in the device of FIG. 1.

A liquid conduit 58 is formed through the body 16 immediately below the Q-ring 52. A short passageway 60 (shown in more detail in FIG. 2) is formed between the lower end of the cavity 22 and the conduit 58 and is aligned with the orifice 53. The cross-sectional configuration of the passageway 60 is tapered and sized to be only slightly larger than the conical tip 48 when the piston 24 is urged downwardly by the spring 38 so as to close the orifice 53. With the piston 24 urged downwardly as shown in FIG. 2, the point 50 rests within the conduit 58. The liquid conduit 58 includes suitably threaded end portions 62 which receive a tube 64 adapted to carry pressurized wash liquid and a tube 66 which is in turn connected to a probe that is adapted to aspirate samples and/or reagents in an otherwise conventional fashion.

Pressurized gas for use with device 10 is supplied by a tube 68 to the solenoid operated valve 14. The tube 68 is connected to an inlet port 70. An outlet port 72 is connected via a tube 74 and a threaded connector 76 to the injector 12. The valve 14 also includes a vent port 78. The valve 14 is connected via wires 80 to a source of electric power for controlling the operation of the valve 14 and thus a device 10 as is described more fully hereinbelow. The valve may be a three-way normally closed valve, part number 11-13-3-BV-12 manufactured by Pneutronics, although other suitable valves will be readily apparent to those skilled in the art.

The threaded connector 76 is received by a threaded portion 82 of a conduit 84 which is in communication with the cavity 22. More particularly, the conduit 84 is in communication with the portion of the cavity 22 between the diaphram 36 and the O-ring 40. This portion of the cavity 22, hereinafter referred to as the actuating chamber 86, is also connected by a small restricted conduit 88 to a threaded portion 90. Another threaded portion 92 forms a portion of a conduit 94 in communication with the portion of the cavity 22 between the O-ring 40 and the Q-ring 52, hereinafter referred to as the low-pressure chamber 96.

A tube 98 connects together and provides gas communication between the conduits 88 and 94. The tube 98 includes a Y-connector 100, one branch of which is connected via a tube 102 to a vent 104. The vent 104 may take the form of a variable restrictor providing a variable or controllable orifice size for controllably bleeding gas from the tube 98 to atmospheric pressure. The tube 98 may also include an in-line fixed orifice restrictor 106 for restricting the flow of gas from the tube 98 to the vent 104. The tube 98 may further include a check valve 108 which prevents back flow of gas liquid from the low-pressure cavity 96 through the tube 98.

Turning now to the operation of a device 10, wash liquid is provided through the tube 64 to the conduit 58 and in turn to the tube 66. The wash liquid may comprise, for example, deionized water supplied at about ten psig. With the device 10 in a non-operating state, liquid may flow through the conduit 58 and tube 66 to, for example, a sample and/or reagent transfer probe. Such probes and the use thereof are well known in the art.

Pressurized gas is applied to the valve 14 via the tube 68. With the valve 14 de-energized, the inlet port 70 is closed and the outlet port 72 is connected to and is in communication with the vent port 78. Under these conditions, the actuating chamber 86 is vented to atmospheric pressure and the spring 38 urges the shaft 26 downwardly, pressing the conical tip 48 tightly against the orifice 53. In this configuration, the point 50 is disposed slightly within the conduit 58 as illustrated particularly in FIG. 2.

To operate the device 10, a control signal is applied to the valve 14 on the wires 80 to thereby energize the valve 14. When energized, the vent port 78 is closed and the inlet port 70 is connected to the outlet port 72 to enable pressurized gas in the tube 68 to be passed into the actuating chamber 86. The gas pressure within the actuating chamber 86 acts against the diaphragm 36 to displace the piston 24 against the bias of the spring 38, moving the conical tip 48 out of the orifice 53. Pressurized gas is also conducted through the restricted conduit 88, tube 98, check valve 108 and conduit 94 into the low-pressure chamber 96.

It is believed that with the orifice 53 opened and gas supplied to the low-pressure chamber 96, an oscillating or pulsating action takes place within the chamber 96. More particularly, gas in the chamber 96 with a pressure greater than the liquid pressure in the conduit 58 is forced into the conduit 58 to form a gas bubble, simultaneously decreasing gas pressure within the chamber 96. With the bubble formed, the decreased gas pressure allows liquid to flow past the orifice 53. As the liquid flows past the orifice 53, gas pressure again builds in the chamber 96 until it is sufficient to form another bubble in the conduit 58. Gas under pressure is then forced into the conduit 58 to form the next gas bubble. This oscillating or pulsating action continues to entrain gas bubbles in the liquid flowing through the conduit 58.

Regardless of the particular fluid dynamics taking place in the device 10, the device 10 rapidly injects discrete gas bubbles into the liquid flowing through the conduit 58. By adjusting the vent 104, the size and number of bubbles injected into the liquid stream in the conduit 58 may be readily adjusted. In the embodiment disclosed herein, the pressure applied to the tube 68 and thus to the actuating chamber 86 is approximately 25 psig. The gas vented to atmosphere through the vent 104 and the gas injected into the liquid flowing in the conduit 58 (whether in accordance with dynamic relationship just described or by means of some unknown relationship) reduces the average gas pressure in the low-pressure chamber 96 (as may be read, for example, with a mechanical pressure gauge) to approximately 14 psig.

To terminate bubble generation, the signal on the wires 80 is removed from the solenoid valve 14. The valve closes, again closing the inlet port 70 and connected the outlet port 72 to the vent port 78. Gas pressure within the actuating chamber 86 immediately decreases, allowing the spring 38 to push the piston 24 downwardly as viewed in the figure, coming to rest with the conical tip 48 resting within the orifice 53. The bubble injection immediately stops, allowing liquid free of bubbles to continue to flow through the conduit 58. Also, as soon as gas flow through the conduit 98 stops, the check valve 108 closes, holding pressurized gas in the low-pressure chamber 98 until the device 10 is again placed into operation.

The device 10 acts very quickly and, in response to the signals on the wires 80, can generate bursts of bubbles injected into the liquid conduit 58 for as little as one second or less. Due to the speed with which the device 10 both begins and terminates bubble generation, the duration of the bubble injection can be precisely controlled. These bubbles may travel through the tube 66 to a probe (not shown) to greatly improve the cleaning accomplished by the liquid.

Because a simple on-off signal is required to activate the device 10, more complicated driving electronic circuitry is eliminated as compared to the pulsed prior art gas injection valve. The mechanical simplicity of the device 10 results in a bubble injection device of considerably longer life than the gas injection valves described above yet which can easily inject bubbles into liquid flowing in the conduit 58 at rates in excess of 100 bubbles/second. Further, by adjusting the vent 104, the size and distribution of gas bubbles injected into the liquid flow is easily controlled. Furthermore, the close proximity of the orifice 53 to the conduit 58 and the very small volume of the passageway 60 with the tip 48 in place essentially eliminates dead volume from the liquid path through the device 10. The gas pressure maintained in the low-pressure chamber 96 by the check valve 108 when the device 10 is not operating helps keep liquid from leaking into the low-pressure chamber 96 and provides a ready supply of pressurized air to promptly begin bubble generation when the valve 14 is energized.

Thus, the device 10 represents a simple yet substantial improvement over prior bubble injection devices and techniques.

The present invention is not to be limited by the detailed description set forth hereinabove but is to be afforded the full range of the appended claims and all equivalents thereto.

What is claimed is:

1. A device for generating a plurality of gas bubbles in a liquid, comprising:
   a conduit having a passageway adapted to carry the liquid;
   a first gas chamber proximate the conduit;
   an orifice formed between the first gas chamber and the conduit;
   a valve member adapted to seat against and close the orifice, the orifice being in a wall to the conduit whereby the valve member is adjacent the passageway;

a gas inlet adapted to connect the first gas chamber to a supply of pressurized gas; and means for actuating the valve member between a closed position wherein the valve members seats against and closes the orifice and an open position wherein the valve member opens the orifice between the first gas chamber and the conduit.

2. A device as claimed in claim 1 wherein the valve is movable between a position partly in the passageway when the orifice is closed and a position removed from the passageway when the orifice is opened, the valve member in the opened position being withdrawn towards the first chamber.

3. A device as claimed in claim 1 including a circular seal between the first chamber and the orifice, the seal being adapted selectively to engage and disengage about the valve member.

4. A device as in claim 1 wherein the means for actuating the valve member includes a second gas chamber, a diaphragm responsive to gas pressure in the second gas chamber, means for coupling the diaphragm to the valve member, a gas inlet adapted to connect the second gas chamber to a controllable supply of pressurized gas, and means for biasing the valve member towards the closed position.

5. A device as in claim 4 wherein the device includes a second conduit forming a gas flow path between the gas inlet and the second chamber.

6. A device as in claim 5 wherein the second conduit includes check valve means for preventing backflow of fluid from the first chamber through the second conduit.

7. A device as in claim 1 wherein the orifice is formed to substantially conform to the shape of the valve member.

8. A device as claimed in claim 7 wherein the valve includes a conical leading end, and the orifice includes a mating tapered cross-sectional configuration.

9. A device as in claim 1 including vent means from the first gas chamber for selectively releasing a portion of the gas.

10. A device as in claim 9 wherein the vent means is variable for adjusting the number and size of bubbles generated in the liquid.

11. A device for generating a plurality of gas bubbles in a liquid, comprising:
a conduit adapted to carry the liquid;
a first gas chamber proximate the conduit;
an orifice formed between the first gas chamber and the conduit;
a valve member adapted to seat against and close the orifice;
a gas inlet adapted to connect the first gas chamber to a supply of pressurized gas;
means for actuating the valve member between a closed position wherein the valve member seats against and closes the orifice and an open position wherein the valve member opens the orifice between the first gas chamber and the conduit, wherein the means for actuating the valve member includes a second gas chamber, a diaphragm responsive to gas pressure in the second gas chamber, means for coupling the diaphragm to the valve member, a gas inlet adapted to connect the second gas chamber to a controllable supply of pressurized gas, means for biasing the valve member towards the closed position; and
a second conduit forming a gas flow path between the gas inlet and the second chamber, wherein the second conduit includes vent means between the first and second gas chambers for releasing a portion of the gas from the second conduit.

12. A device as in claim 11 wherein the vent means is variable for adjusting the number and size of bubbles generated in the liquid.

13. A device as in claim 11 wherein the second conduit includes a check valve for preventing backflow of fluid from the first chamber through the second conduit.

14. A device as in claim 11 wherein the device further includes valve means for controllably applying pressurized gas to and releasing pressurized gas from the second chamber.

15. A device as in claim 14 wherein the valve means includes an electrically controled solenoid valve.

16. A device for generating a plurality of gas bubbles in a liquid, comprising:
a conduit having a passageway adapted to carry the liquid;
a first gas chamber proximate the conduit;
an orifice formed between the first gas chamber and the conduit;
a valve member adapted to seat against and close the orifice, the orifice being in a wall to the conduit whereby the valve member is adjacent the passageway;
a gas inlet adapted to connect the first gas chamber to a supply of pressurized gas;
a second gas chamber, a diaphragm responsive to gas pressure in the second gas chamber, means for coupling the diaphragm to the valve member, a gas inlet, and means for biasing the valve member towards a closed position wherein the valve member seats against and closes the orifice;
valve means for controllably applying pressurized gas to and releasing pressurized gas from the second chamber gas inlet; and
a second conduit forming a gas flow path between the first chamber gas inlet and the second chamber.

17. A device for generating a plurality of gas bubbles in a liquid, comprising:
a conduit adapted to carry the liquid;
a first gas chamber proximate the conduit;
an orifice formed between the first gas chamber and the conduit;
a valve member adapted to seat against and close the orifice;
a gas inlet adapted to connect the first gas chamber to a supply of pressurized gas;
a second gas chamber, a diaphragm responsive to gas pressure in the second gas chamber, means for coupling the diaphragm to the valve member, a gas inlet, and means for biasing the valve member towards a closed position wherein the valve member seats against and closes the orifice;
valve means for controllably applying pressurized gas to and releasing pressurized gas from the second chamber gas inlet; and
a second conduit forming a gas flow path between the first chamber gas inlet and the second chamber, wherein the second conduit includes vent means between the first and second gas chambers for releasing a portion of the gas from the second conduit.

18. A device as in claim 17 wherein the orifice is formed to substantially conform to the shape of the valve member and the orifice includes a valve seat adapted to receive the valve member when the valve member is in the closed position.

19. A device for generating a plurality of gas bubbles in a liquid, comprising:
a conduit having a passageway adapted to carry the liquid;
a first gas chamber proximate the conduit;
an orifice formed between the first gas chamber and the conduit;
a valve member adapted to seat against and close the orifice, the orifice being in a wall to the conduit whereby the valve member is adjacent the passageway;
a gas inlet adapted to connect the first gas chamber to a supply of pressurized gas; and means for actuating the valve member between a closed position wherein the valve members seats against and closes the orifice and an open position wherein the valve member opens the orifice between the first gas chamber and the conduit, and valve means for controllably applying pressurized gas to and releasing pressurized gas from the chamber.

20. A device as in claim 19 wherein the valve means includes an electrically controlled solenoid valve.

21. A device for generating a plurality of gas bubbles in a liquid, comprising:
a conduit having a passageway adapted to carry the liquid;
a first gas chamber proximate the conduit;
an orifice formed between the first gas chamber and the conduit;
a valve member adapted to seat against and close the orifice, the orifice being in a wall to the conduit whereby the valve member is adjacent the passageway;
a gas inlet adapted to connect the first gas chamber to a supply of pressurized gas;
second gas chamber means for actuating the valve member between a closed position wherein the valve member seats against and closes the orifice between the first gas chamber and the conduit; and
valve means for controllably applying pressurized gas to and releasing pressurized gas from the second gas chamber.

22. A device as in claim 21 wherein the valve means includes an electrically controlled solenoid valve.

23. A device for generating a plurality of gas bubbles in a liquid comprising:
a conduit having a passageway adapted to carry the liquid;
a first gas chamber proximate the conduit;
an orifice formed between the first gas chamber and the conduit;
a valve member adapted to seat against and close the orifice, the orifice being in a wall to the conduit whereby the valve member is adjacent the passageway;
a gas inlet adapted to connect the first gas chamber to a supply of pressurized gas;
means for actuating the valve member between a closed position wherein the valve member seats against and closes the orifice and an open position wherein the valve member opens the orifice between the first gas chamber and the conduit, the means for actuating the valve member including a second gas chamber, a diaphragm responsive to gas pressure in the second gas chamber, means for coupling the diaphragm to the valve member, a gas inlet adapted to connect the second gas chamber to a controllable supply of pressurized gas, and means for biasing the valve member towards the closed position, the biasing means being located on a side of the diaphragm remote from the valve member.

24. A device as in claim 23 wherein the biasing means is a spring located in chamber formed on the remote side of the diaphragm, the spring acting to urge the diaphragm oppositely to pressure in the second gas chamber.

25. A device as in claim 24 including check valve means for preventing backflow of fluid from the first chamber to the gas inlet connected to the first gas chamber.

26. A device as in claim 24 including valve means for controllably applying pressurized gas to and releasing pressurized gas from the second chamber.

27. A device as in claim 26 wherein the valve means includes an electrically controlled solenoid valve.

28. A device as in claim 26 wherein the orifice includes a tapered cross-sectional configuration formed to conform substantially to a conical leading end of the valve member and the orifice includes a valve seat adapted to receive the valve member when the valve member is in the closed position.

29. A device for generating a plurality of gas bubbles in a liquid comprising:
a conduit adapted to carry the liquid;
a first gas chamber proximate the conduit;
an orifice formed between the first gas chamber and the conduit;
a valve member adapted to seat against and close the orifice, the orifice being in a wall of the conduit whereby the valve member is adjacent the passageway;
a gas inlet adapted to connect the first gas chamber to a supply of pressurized gas;
means for actuating the valve member between a closed position wherein the valve member seats against and closes the orifice and an open position wherein the valve member opens the orifice between the first gas chamber and the conduit, the means for actuating the valve member including a second gas chamber, a diaphragm responsive to gas pressure in the second gas chamber, means for coupling the diaphragm to the valve member, a gas inlet adapted to connect the second gas chamber to a controllable supply of pressurized gas, and means for biasing the valve member towards the closed position; and
a second conduit forming a gas flow path to the gas inlet wherein the second conduit includes check valve means between the first gas chamber and the gas inlet.

30. A device for generating a plurality of gas bubbles in a wash liquid for a chemical clinical analyzer comprising:
a conduit having a passageway adapted to carry the liquid;
a first gas chamber proximate the conduit;
an orifice formed between the first gas chamber and the conduit;

a valve member adapted to seat against and close the orifice, the orifice being in a wall to the conduit whereby the valve member is adjacent the passageway;

a gas inlet adapted to connect the first gas chamber to a supply of pressurized gas; and means for actuating the valve member between a closed position wherein the valve member seats against and closes the orifice and an open position wherein the valve member opens the orifice between the first gas chamber and the conduit, the means for actuating the valve member including a second gas chamber, a diaphragm responsive to gas pressure in the second gas chamber, means for coupling the diaphragm to the valve member, a gas inlet adapted to connect the second gas chamber to a controllable supply of pressurized gas, and means for biasing the valve member towards the closed position such that on opening of the valve member gas bubbles are formed in the wash liquid in the conduit.

31. A method for generating a plurality of gas bubbles in a wash liquid for a chemical clinical analyzer comprising:

carrying the wash liquid in a conduit having a passageway;

forming an orifice between the conduit and a first gas chamber proximate the conduit;

seating a valve member against the orifice for closing the orifice, the orifice being in a wall to the conduit whereby the valve member is adjacent the passageway;

connecting a gas inlet to the first gas chamber to a supply of pressurized gas;

actuating the valve member between a closed position wherein the valve member seats against and closes the orifice and an open position wherein the valve member opens the orifice between the first gas chamber and the conduit;

actuating the valve member through a second gas chamber, a diaphragm responsive to gas pressure in the second gas chamber, and a coupling of the diaphragm to the valve member;

connecting a gas inlet to the second gas chamber to a controllable supply of pressurized gas;

biasing the valve member towards the closed position; and opening of the valve member to form gas bubbles in the wash liquid conduit.

* * * * *